US012731681B2

(12) United States Patent
Wenzel et al.

(10) Patent No.: US 12,731,681 B2
(45) Date of Patent: Sep. 8, 2026

(54) CLOSED LOOP DEVICE SETTING ADJUSTMENT FOR MEDICAL DEVICES

(71) Applicant: BIOTRONIK SE & Co. KG, Berlin (DE)

(72) Inventors: Matthias Wenzel, Bremen (DE); Miro Selent, Nuthetal (DE); Georg Nollert, Strasslach (DE); Dominic Wist, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 409 days.

(21) Appl. No.: 18/549,190

(22) PCT Filed: Feb. 22, 2022

(86) PCT No.: PCT/EP2022/054373
§ 371 (c)(1),
(2) Date: Sep. 6, 2023

(87) PCT Pub. No.: WO2022/189137
PCT Pub. Date: Sep. 15, 2022

(65) Prior Publication Data

US 2024/0170144 A1 May 23, 2024

(30) Foreign Application Priority Data

Mar. 10, 2021 (EP) .................................... 21161651

(51) Int. Cl.
*G16H 40/40* (2018.01)
*G16H 10/60* (2018.01)
(Continued)

(52) U.S. Cl.
CPC ............. *G16H 40/40* (2018.01); *G16H 10/60* (2018.01); *G16H 20/00* (2018.01); *G16H 50/70* (2018.01)

(58) Field of Classification Search
CPC ........ G16H 40/40; G16H 10/60; G16H 20/00; G16H 20/30; G16H 20/60; G16H 50/70
See application file for complete search history.

(56) References Cited

U.S. PATENT DOCUMENTS

| | | | |
|---|---|---|---|
| 2003/0204415 | A1 | 10/2003 | Knowlton |
| 2012/0232930 | A1 | 9/2012 | Schmidt et al. |

(Continued)

OTHER PUBLICATIONS

International Search Report (PCT/ISA/210) and Written Opinion (PCT/ISA/237) mailed on May 18, 2022, by the European Patent Office as the International Searching Authority for International Application No. PCT/EP2022/054373. (12 pages).

*Primary Examiner* — Mong-Shune Chung
(74) *Attorney, Agent, or Firm* — Buchanan Ingersoll & Rooney PC

(57) ABSTRACT

The present invention relates to an apparatus and method for determining settings of a medical device associated with a patient. The apparatus comprises a) means for receiving a patient-specific value of a least one parameter; b) means for generating a profile for the patient based on the patient-specific value; and c) means for determining a setting of at least one operating parameter of the medical device based on a comparison of the profile for the patient with stored profiles of the patient and/or of other patients in a storage medium, each stored profile comprising a stored setting of the at least one operating parameter and a stored patient-specific value of the at least one parameter.

10 Claims, 1 Drawing Sheet

(51) Int. Cl.
*G16H 20/00* (2018.01)
*G16H 50/70* (2018.01)

(56) References Cited

U.S. PATENT DOCUMENTS

| | | | | |
|---|---|---|---|---|
| 2014/0324446 | A1 | 10/2014 | Slotman | |
| 2015/0161331 | A1 | 6/2015 | Oleynik | |
| 2016/0275259 | A1* | 9/2016 | Nolan | G16H 20/30 |
| 2019/0035495 | A1* | 1/2019 | Birtwhistle | G16H 40/40 |
| 2019/0108898 | A1* | 4/2019 | Gulati | G16H 10/60 |
| 2020/0121544 | A1* | 4/2020 | George | G16H 20/70 |
| 2021/0287810 | A1* | 9/2021 | Franz | G16H 40/67 |

* cited by examiner

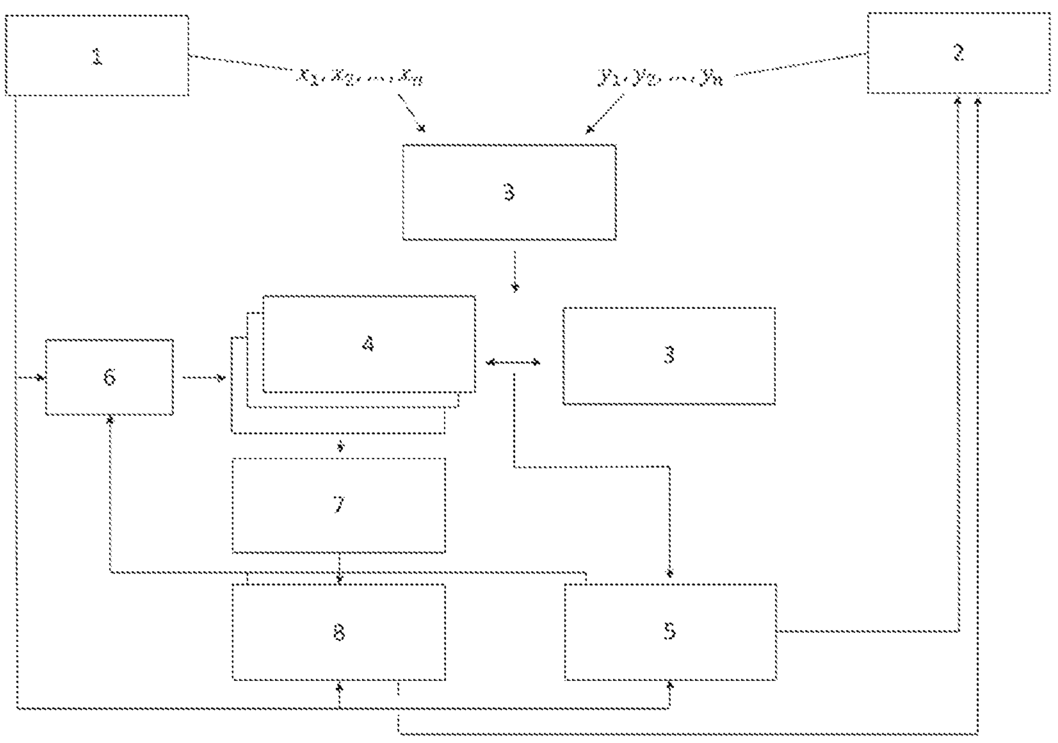
1
2
$x_1, x_2, \ldots, x_n$
$y_1, y_2, \ldots, y_n$
3
4
3
6
7
8
5

CLOSED LOOP DEVICE SETTING ADJUSTMENT FOR MEDICAL DEVICES

CROSS-REFERENCE TO RELATED APPLICATIONS

This application is the United States National Phase under 35 U.S.C. § 371 of PCT International Patent Application No. PCT/EP2022/054373, filed on Feb. 22, 2022, which claims the benefit of European Patent Application No. 21161651.1, filed on Mar. 10, 2021, the disclosures of which are hereby incorporated by reference herein in their entireties.

TECHNICAL FIELD

The present disclosure relates to methods and apparatuses for determining settings of a medical device associated with a patient. In particular, the present disclosure relates to a closed loop operation for adjusting medical devices in the field of therapeutic and/or diagnostic applications.

BACKGROUND

A variety of different diagnostic and therapeutic devices are available in cutting-edge medicine for therapy, e.g., to increase the wellbeing of a patient during a therapy or to allow state-of-the-art diagnostics.

Such devices benefit from precise adjustment of their settings to the individual patient. However, this is typically highly labor-intensive which raises costs. Moreover, lengthy adjustments by medical staff may contribute to increase emotional stress not only of patients but also of doctors and nursing staff. A decrease of the time spent for adjustment may on the other hand deteriorate diagnostics and therapy, which may not be perfectly individually adjusted anymore according to the needs of the patient and which may not take into account, e.g., the individual patient chart adequately. This leads to the drawback that the full potential of a diagnostic and/or a therapy may not be unfolded. What is more, the state of a patient may evolve or abruptly change over time which—for individualizing treatment or diagnostics by a medical device—may require re-adjustment of the settings of the medical device. Frequently re-visiting a hospital or local doctor to perform these re-adjustments would be cumbersome and further increase costs. Moreover, even if such visits were scheduled periodically, this may not be sufficient to address sudden changes of a patient's state which may even put the live of the patient at risk if no immediate action of the medical staff is taken to counteract.

Therefore, there is a need to improve the known ways to adjust settings of medical devices.

The present disclosure is directed toward overcoming one or more of the above-mentioned problems, though not necessarily limited to embodiments that do.

SUMMARY

According to an aspect of the present disclosure, the above need is at least partly met by an apparatus for determining settings of a medical device associated with a patient, which comprises means for receiving a patient-specific value of a least one parameter and means for generating a profile for the patient based on the patient-specific value. Moreover, the apparatus may comprise means for determining a setting of at least one operating parameter of the medical device based on a comparison of the profile for the patient with stored profiles of the patient and/or of other patients in a storage medium. Each stored profile may comprise a stored setting of the at least one operating parameter and a stored patient-specific value of the at least one parameter.

Hence, it may be enabled to take into account the individual patient's state, by means of patient-specific values of at least one parameter, and initialize and/or adjust the setting of the medical device based thereon. The at least one parameter may generally characterize the current state of the patient, e.g., it may include direct parameters characterizing the (health) state of the patient (e.g., blood pressure, heart rate) and/or indirect parameters associated therewith (e.g., humidity or temperature of the patient's environment), or it may relate to general patient data (e.g., date of birth, blood type). Stored profiles with e.g., positively confirmed settings for various patient states may be accessed for that matter, which may include positively confirmed settings that had turned out to be beneficial for the present state or at least for a similar state (e.g., as determined based on a comparison of the patient-specific value of the at least one parameter with the corresponding values stored in at least one stored profile). These settings (or: the corresponding stored setting of the at least one operating parameter) may then be determined as the setting, and the medical device may be adjusted accordingly, e.g., in a fully automated manner. Hence, a patient specific adjustment of medical devices may be enabled, minimizing the required actions of medical staff.

Such adjustment may even allow a patient to leave hospital early as it may allow for further caretaking at home, in an environment the patient is familiar with. This may also increase the general wellbeing and satisfaction of the patient.

What is more, and as will be outlined in further detail below, an updated profile may be generated for the patient based on the setting, and—depending on the actual evolution of the patient's state—this profile may then be added as a further stored profile to the storage medium, such that it will be available for further adjustment of medical devices of the patient and/or other patients. Hence, a self-learning apparatus may be provided. Such a procedure may be performed in closed loop operation with the goal of maximizing the wellbeing of the patient while minimizing the required efforts of the medical staff.

The apparatus may in particular be used for medical applications such as a therapy and/or a diagnosis of a patient. A therapy may be understood as an intervention into a health state of the patient, which preferably improves the health state of the patient, e.g., by adjusting a dose of a pharmaceutical, by generating a clock like signal as it may be beneficial for pacemakers, etc. A diagnosis may e.g., refer to an imaging method which may e.g. involve radiopharmaceuticals for increasing a contrast ratio (e.g., the ratio of an imaging brightness of bones vs. an imaging brightness of soft tissue). The apparatus may thus be used to adjust the dose of the radiopharmaceutical to achieve the desired contrast ratio. Or it may generally be used to adjust settings of a diagnostic device to optimize the quality of diagnostics.

Optimizing in the context of the present application may be understood as (iteratively) choosing the settings of a medical device such that a wellbeing of the patient is improved.

The optimization may be patient-specific, i.e., different patients may require different settings. An optimized health state of a patient may be based on at least one value of an objective parameter (e.g., a target blood pressure of 120/80 mmHg and/or a resting heart rate of 60 beats per minute) or may be based on at least one value of a subjective parameter (e.g., an individual feeling of a patient in response to an adjustment of a setting of a medical device, which may refer to a level one or more of pain, vertigo, nausea, etc.; and/or feedback by medical staff).

The apparatus may optionally include means for receiving settings of at least one operating parameter of the medical device. This means may be implemented as a first interface. The means for receiving a patient-specific value of a least one parameter may be implemented with the same first interface and/or a distinct interface. An interface may generally refer to a hardware and/or software interface. A hardware interface may be understood as e.g., a USB connection, an ethernet connection or any other suitable hardware interface which allows a reception of at least one operating and/or a reception of a patient-specific value of at least one parameter. The hardware interface may be based on a wireless (e.g., Wi-Fi, 5G, LTE, Bluetooth or any other suitable standard and/or air interface) and/or a wired connection (e.g., a copper wired connection). Additionally or alternatively, the interface may also be embedded in software and may relate to various protocols (e.g., IP, TCP, UDP, I2C, GPIO, etc.). The software interface may further be based on the communication of web sockets.

For example, the apparatus may be implemented (e.g., embedded) in a server- or cloud-based system, e.g., comprising the storage medium (such as a database and/or a blockchain). The apparatus may then communicate (telemetrically and/or continuously and/or bidirectionally) with the medical device (e.g., a pacemaker, or an implantable defibrillator, ICD), e.g., to receive patient-specific values of a parameter as determined by the medical device. The apparatus may continuously optimize settings of the medical device customized for the individual patient. The cloud-based system may be understood as a software-as-a-service (SaaS) and/or an infrastructure-as-a-service (IaaS) implementation. The server system may provide hardware and/or software resources to perform the functions of the present disclosure. Such resources may comprise at least one transient and/or non-transient storage medium and/or at least one processor and/or at least one medium for communication (e.g., one or more interfaces as outlined above). The server system may be implemented as part of a hospital information system and/or a remote server system (e.g., in a datacenter which may be accessible over the internet).

Additionally, the apparatus may communicate with the patient (e.g., a smartphone app on the patient's smartphone) and/or medical staff (e.g., a smartphone app and/or a communication program in a hospital network). For communication, one or more of the above interfaces may be used, e.g., via the internet.

Further, it is also conceivable that the apparatus is implemented e.g., in a mobile device, such as a smartphone, adapted to be carried by the patient. The apparatus may then additionally be adapted to communicate with a server-based system which may comprise the storage medium in which the stored profiles are stored.

It is also conceivable that the medical device is comprised by the apparatus, e.g., the apparatus may be implemented by one or more processors in the medical device. The apparatus/medical device may then be adapted to communicate with a server-based system which may comprise the storage medium in which the stored profiles are stored. The apparatus may e.g., be part of an implant (e.g., as a system on a chip (SoC) or any other integrated circuit (IC)). Alternatively it may be embedded in the implant by means of an implementation as a respective software (method), e.g., on a EPROM, EEPROM or FPGA.

The patient-specific value of a least one parameter may, for example, relate to one or more cardiovascular parameters (e.g., blood pressure, pulse rate) and/or cardio pulmonal parameters (e.g., a blood oxygen concentration), body temperature or any other patient-specific vital parameter. It may be measured by means of the medical device to be adjusted and provided to the apparatus. However, additionally or alternatively, it may also be based on entries in a database, a patient chart (e.g., at least one of the above-mentioned parameters and/or further a detailed list of the administered medication, potential allergies and intolerances of the patient, an anamnesis, reports regarding earlier hospitalization, etc.). Further data sources may comprise a hospital information system (e.g., all information processing devices and systems in a hospital which may e.g., comprise doctors' letters, surgery reports, etc.), clinical data sets (e.g., information related to the health state of the patient (e.g., blood values) and further parameters which cannot directly be gained by means of sensors (e.g., the subjective wellbeing of the patient)). Additionally or alternatively, patient-specific data may also be retrieved over the internet (e.g., a GPS location of a patient and related environmental data (e.g., a temperature value, a humidity value, etc.)) and/or from a blockchain. The latter may provide the beneficial effect of providing a decentralized data storage medium which ensures data integrity (e.g., data consistency (data without contradiction)) and a decreased vulnerability (i.e., the chances for intrusion attacks and/or data losses and/or data piracy based on inadvertent and/or criminal activities may be minimized). Retrieving data over the internet may provide the advantage of correlating the at least one parameter (associated with the health of patient) to the current context of the patient, e.g., a temporary stay in a hot climate zone which may be determined based on GPS data (which may be determined by a smartphone or a smartwatch or any other suitable device) and the corresponding weather information which may be retrieved over the internet.

The patient-specific value of the at least one parameter may also be retrieved from a mobile device, which is not necessarily a medical device, e.g., by means of a smartphone app or a wearable (e.g., a smartwatch or a step counter embedded in a (sports) shoe). The mobile device may not only retrieve indirect patient-specific parameters (e.g., environmental parameters, such as a temperature and/or a humidity value) but also, e.g., additional sensor data, e.g., that directly characterize the health state (e.g., heart rate), such that further parameters not obtainable from the medical device may be used.

The patient-specific value of the at least one parameter may be received from the same medical device that is to be set, or may be received from one or more different medical devices (e.g., an implanted device such as a pacemaker, a defibrillator a cochlea implant, etc.). In the latter scenario, for example, the setting may relate to a respirator (and settings of at least one operating parameter may be received from the respirator), whereas a value of a temperature measurement and/or an analysis of an electrocardiogram (ECG) may be received from different medical devices. This may provide the advantage of being able to correlate a variety of parameters which may be used to characterize the health state of the patient.

The patient-specific value of a least one parameter may be based on first, second and/or third rank data. First rank data sets may refer to the above-mentioned parameters which are directly related to the patient (e.g., a value of the blood pressure, humidity). Second rank data may relate to parameters which are based on first rank data but which are further processed, e.g., to determine heart-specific parameters in dependence on the blood pressure or the calculation of a risk for heart attacks in dependence on markers which can be determined from the investigation of blood samples (e.g., troponin). Third rank data may be based on second rank data but further processed, i.e., on a higher level of abstraction compared to second and first rank data.

Generating a patient-specific profile may (in an exemplary manner) be understood as combining the received patient-specific value(s) of at least one parameter (e.g., to a virtual flashcard). The profile may further be assigned with a patient-specific ID (which may be anonymous). Equipping the generated profile (the virtual flashcard) with a patient-specific ID, may further provide the beneficial effect of a transparent assignment of the generated profile to a particular patient. Furthermore, the generated profile may then not only comprise a single temporary snapshot of the state of the patient (which may be represented by the received patient-specific value(s) of at least one parameter) but it may comprise several snapshots of the state of the patient (which may be represented by the received patient-specific value of at least one parameter). The latter may then allow to review the temporal evolution of the state of the patient, possibly with a high frequency and/or quasi-continuously (with updates e.g., every day, every hour, every minute, every second, etc.). Alternatively, it may also be possible that a new patient-specific profile is generated for each of the one or more snapshots of the health state of the patient. In such an application, the generated patient-specific profiles may ex post be assignable to a particular patient by means of the patient-specific ID. Once a setting of the at least one operating parameter of the medical device is determined (or such setting is otherwise received by the apparatus), the profile may be updated with the setting.

In some examples, the generated patient-specific profile may be stored for later usage. Storing may refer to storing the patient specific profile in a transient (e.g., a random access memory (RAM), a cache memory) and/or a non-transient storage medium (e.g., hard drive, a flash memory, a CD, DVD, etc.) and/or a database, a blockchain, etc.

The stored profiles may be historic profiles, i.e., profiles which were accumulated in the past during the therapy and/or the diagnosis of the same and/or at least one other patient (e.g., evidence-based, associated with a positivity value concerning their effect, e.g., whether the setting of the profile was beneficial or detrimental, possibly with a value indicating a likelihood).

The comparison of the profile for the patient with stored profiles of the patient and/or of other patients in a storage medium may be directed to comparing a single patient-specific value of at least one parameter to a stored patient-specific value of the at least one parameter. Alternatively, it may also be possible to compare the patient-specific values of more than one parameter to stored corresponding values of these parameters. Additionally or alternatively, the patient-specific value of a parameter may also be represented as a vector. It may be possible that each row of the vector may represent a temporal snapshot of the patient-specific value of the at least one parameter which may thus facilitate the tracking of temporal evolutions of the at least one parameter.

The stored profiles may have been generated based on patient-specific data sets which are related to the same patient and/or may be based on patient-specific data sets of at least one other patient. The setting of the at least one operating parameter may refer to a setting of the at least one operating parameter to which the medical device may be altered subsequent to the determination of the setting of the at least one operating parameter or it may relate to an initialization value.

Additionally, the stored profiles may also be used to interpolate data sets which were not retrieved continuously, e.g., due to communication errors or organizational issues (e.g., a blood value which is not determined periodically due to holidays or increased workload).

The apparatus may be based on techniques of artificial intelligence (AI). For example, the means for determining may be implemented using techniques of AI. The apparatus may also be understood as a self-learning system, in particular, as it may be possible to suggest a setting for the medical device based on the current patient-specific value of the at least one parameter (associated with the state of the patient) without any further input, e.g., from medical staff and/or the patient.

The comparison may also comprise the determination of a similarity between the profiles and, in particular, the determination of a rank of similarity. A rank "1" similarity may relate to a similarity or even identity of all relevant patient-specific parameter values in the profile which are involved for the comparison. Which values are considered as relevant values may be defined by the specific application, e.g., whether the medical device relates to a pacemaker and/or an implantable defibrillator. As an example, if the present invention is used to set a pacemaker, parameters (which may be comprised by the profile) which may indicate a broken bone may not be regarded as relevant. However, if a previous heart attack has been documented in the anamnesis, such information may be considered as highly relevant. Rank "two", "three", . . . to rank "n" similarities may refer to a similarity in all but one, two, . . . n−1 parameter values. This distinction of the profiles may allow the determination whether a patient with a similar health state has already been documented (and stored). For example, profiles with "rank 1", "rank 2" etc. compared to the generated profile for the patient may be displayed to the medical staff, together with statistical data concerning a frequency of certain deviations in the parameter values and/or the corresponding settings.

The medical device may be configured as at least one of: a device which is implantable or implanted to the patient, a device wearable or worn by the patient and/or a device connectable or connected to the patient. The medical device may be used for diagnostic and/or therapeutic applications. An implantable device may refer to e.g., a pacemaker, etc. A device wearable by the patient may relate to smartphones, smartwatches, a portable ECG, or any other type of sensors (e.g., a step counter in a shoe), a chest strap or any other wearable device. A device connectable to the patient may be a helmet which may be used for monitoring a brain activity (e.g., for monitoring an electroencephalogram (EEG)), a medical device such as e.g., devices for applying an infusion, a medical monitor (e.g., used for the surveillance of at least one vital parameter of the patient).

The parameter may generally be a static parameter (e.g., a birthdate of the patient and/or a blood type) and/or a dynamic parameter (e.g., at least one blood value, a heart rate, etc.).

The means for receiving the one or more patient-specific value may further comprise means for receiving an update of the at least one patient-specific value (and/or repeatedly receiving updates). Hence, the setting may be updated repeatedly, based on the updated at least one patient-specific value.

Repeatedly receiving updates may refer to receiving updates periodically. Periodically receiving updates may relate to receiving updates on a regular time scale, e.g., every second, every minute, every hour, every day, once per year or even longer time scales. Additionally or alternatively, the updates may also be received quasi-continuously, e.g., approximately every day, every hour, every minute or even on shorter timescales etc. In particular, the updates may also be received discontinuously and/or on an irregular time basis, e.g., as a result of an explicit request by e.g., the medical staff and/or the patient. Such a request may be based on a sudden change of the state of the patient. For example, the blood pressure of the patient may be tracked on long time scales (e.g., once per day or once per hour, for the sake of monitoring the state of the patient) and may switch to immediately measuring the blood pressure of the patient and/or repeatedly measuring it in shorter intervals (e.g., every second or every minute), if it is detected that the state of the patient has deteriorated (i.e., the blood pressure may have harmfully increased). After a normalization of the blood pressure is detected, the frequency of receiving updates may switch back to longer time scales (e.g., to avoid an undue amount of data production).

The apparatus may further comprise means for updating the profile for the patient based on the update of the at least one patient-specific value. The apparatus may further comprise means for determining a second setting of the at least one operating parameter based on a comparison of the updated profile for the patient with stored profiles of the patient and/or of other patients in a storage medium, each stored profile comprising a stored setting of the at least one operating parameter and a stored patient-specific value of the at least one parameter. Hence, the setting can iteratively be adjusted to follow the needs by the patient.

The means for determining the setting (second setting) may further comprise means for selecting a stored profile based on a comparison of the stored patient-specific value of the at least one parameter in the stored profile and the value of the at least one parameter in the generated profile (updated profile) for the patient. It may further comprise means for selecting, as the setting (second setting), the stored setting of the at least one operating parameter of the selected stored profile. In other words, a stored profile may be selected if its patient-specific value(s) "match(es)" with the generated profile (updated profile) for the patient. If such match is found, the stored setting of the "matching" stored profile may be selected as the setting (second setting).

For example, the apparatus may further comprise means for calculating a metric for the stored profile, wherein the metric is calculated between the value of the at least one parameter in the generated profile for the patient and the stored patient-specific value of the at least one parameter in the stored profile (this and the following calculations are similarly applicable if a second setting is to be selected).

The calculation of the metric may be performed based on the value of one parameter in the generated profile for the patient and one stored patient-specific value of the at least one parameter in the stored profile. Alternatively, the calculation of the metric may be based on a plurality of patient-specific values. For example, patient-specific values for each of several parameters in the generated profile for the patient and corresponding stored patient-specific values may be used. Additionally or alternatively, also patient-specific values taken at different instances in time may be used for the metric. In case profiles do not relate to single instants in time but include temporal evolution of a patient's state (as outlined above), the metric may relate to a deviation of stored patient-specific values from those in the generated profile for the patient during the course of time. Hence, stored profiles may be identified, based on the metric, which describe a similar trajectory of the state of a patient over time. The calculation of the metric may be based on some or all of the patient-specific values of some or all available parameters of the generated profile and/or the stored profile, respectively. Optionally, it may also be possible to include weighting factors into the calculation of the metric. Such a weighting of one or more parameters may be beneficial to weight certain vital parameters (represented by the weighting factors) which may in particular be harmful to the health state of the patient when exceeding certain intervals (e.g., the blood pressure for patients sensitive to strokes).

The means for calculating may be adapted to calculate a metric for a plurality of the stored profiles, and the means for selecting may be adapted to select a stored profile for which the metric is minimized. Hence, the best "match" may be identified.

The calculation of the metric may be performed for selected stored profiles or may be calculated for all available profiles. For examples, the calculation of the metric may be limited to stored profiles fulfilling certain predetermined conditions. For example, if two or more parameters are available in the generated profile and the stored profiles, the metric may be calculated only for stored profiles with one of the parameters fulfilling a certain predetermined criterion, e.g., the metric may be limited to profiles of patients with similar or same age, of patients having similar diseases (having experienced at least one stroke), etc.

The means for selecting the stored profile may be adapted to select the stored profile, (only) if the metric is below a threshold. The threshold may be a pre-defined value which may be defined by the medical staff and/or the patient and may be understood as a value which defines how close the at least one patient-specific value in a stored profile needs to be to the corresponding at least one value in the corresponding generated profile to interpret a stored profile as a "match". The threshold may be a global value (i.e., identical for all patients) or may be a patient-specific value, which allows an adaption of the selection process according to the individual needs of the patient. This threshold criterion may be applied additionally or alternatively to the selection of the "minimum", as outlined above. For example, a selected minimum may need to be below the threshold in order to be selected. Alternatively, a profile may immediately be selected if its metric is below threshold, regardless of whether there may be a profile with a lower metric value.

It may also be possible, that a setting for the medical device may only be selected, if the patient-specific value of the at least one parameter deviates from a threshold. For example, a second setting may only be selected, if e.g., a pulse rate deviates by more than e.g., 10 bpm from an interval which is defined as "normal" (e.g., a pulse rate between 50-90 bpm at rest). Alternatively and/or additionally, a second setting for the medical device may be selected based on an input of the medical staff and/or the patient. This may e.g., be beneficial if the subjective wellbeing of the patient may change (e.g., due to a suddenly occurring vertigo). The dedicated threshold for the maximum allowable deviation may be patient-specific (by e.g., considering pre-existing diseases) or may be a generic value.

It is therefore a further aspect of the present disclosure to provide an apparatus for determining settings of a medical device associated with a patient, which comprises means for receiving an update of a patient-specific value of a least one parameter (or repeatedly receiving updates). A profile for the patient may be updated based on the updates of the patient-specific value. The apparatus may comprise means for determining a second setting as described herein, which determines a second setting (only) if the patient-specific value exceeds one or more predetermined values. For example, the values may be predetermined as certain deviations (+/−) from an initial value of the patient-specific value.

The apparatus may comprise means for augmenting the generated profile for the patient with at least one further patient-specific value of at least one further parameter, if none of the stored profiles has a metric below the threshold. The apparatus may further be configured with means for calculating an augmented metric for one or more of the stored profiles, wherein the augmented metric may be calculated between the patient-specific values in the augmented profile for the patient and corresponding stored patient-specific values in the stored profile. Such a situation may occur if no stored profile can be found in which the patient-specific value of the at least one parameter is close to the respective stored patient-specific value of the at least one parameter. In other words, based on the generated profile, no "match" can be found. In such case, more data (for at least one further parameter) may be acquired, such that the generated profile may be augmented based thereon. The at least one further parameter may refer to at least one parameter which may be used to explain and/or interpret the discrepancy (e.g., expressed in terms of at least one metric) between the stored profiles and the generated profile for the patient. Such further parameters may e.g., comprise at least one additional health parameter or general patient parameter, and/or at least one environmental parameter (e.g., a temperature value, a humidity value, etc.). In an exemplary scenario, such additional parameters may be beneficial if e.g., the patient specific value of at least one parameter (e.g., of a patient suffering of myocardial failure) strongly deviates from the respective patient-specific parameters in the stored profiles. In such a scenario, the current health state of the patient may not be explained by the stored profiles. However, by augmenting the generated profile for the patient with at least one further patient-specific value of at least one further parameter, e.g., a GPS location of the patient and environmental parameters (e.g., temperature and humidity) at the respective location (said parameters may be incorporated into the augmented profile), the health state of the patient may be explained as at least partially be caused by the environmental conditions, if e.g., the patient is on holiday in a hot climate zone with a rather saturated humidity value. With the thus gained additional knowledge, the metric may be recalculated based on the augmented profile and the stored profiles.

Recalculating the metric may comprise all parameters of the augmented generated profile for the patient, a selection of the parameters or may be based on a single parameter. The recalculating of the metric may comprise all stored profiles or a selection of stored profiles.

In an exemplary embodiment, the apparatus for determining settings of a medical device associated with a patient comprises a) means for receiving a patient-specific value of a least one parameter, b) means for generating a profile for the patient based on the patient-specific value, and c) means for determining a setting of at least one operating parameter of the medical device based on a comparison of the profile for the patient with stored profiles of the patient and/or of other patients in a storage medium, each stored profile comprising a stored setting of the at least one operating parameter and a stored patient-specific value of the at least one parameter. The apparatus further comprises means for calculating a metric for the stored profile, wherein the metric is calculated between the value of the at least one parameter in the generated profile for the patient and the stored patient-specific value of the at least one parameter in the stored profile, wherein the means for calculating is adapted to calculate a metric for a plurality of the stored profiles. Furthermore, the means for selecting is adapted to select a stored profile for which the metric is minimized, wherein the means for selecting the stored profile is adapted to select the stored profile, if the metric is below a threshold. Furthermore, the apparatus comprises means for augmenting the generated profile for the patient with at least one further patient specific value of at least one further parameter, if none of the stored profiles has a metric below the threshold. And the apparatus is further configured with means for calculating an augmented metric for the stored profiles, wherein the augmented metric is calculated between the patient specific values in the augmented profile for the patient and corresponding stored patient-specific values in the stored profiles. The features contained in this embodiment contribute decisively to a solution to the technical problem of simplifying the operation/setting of a medical device (the apparatus) for the user.

The means for selecting may further be adapted to select a stored profile based on a positivity value associated with the stored profile. The positivity value may be associated with a likelihood that the setting of the at least one operating parameter stored in the profile may lead to an increase of a health state of the patient. The likelihood may be expressed as a probability value wherein the probability value may be any value in between 0 and 100%. A value of 100% may indicate that the respective setting of the at least one operating parameter of the stored profile may lead to an increase of the health state of the patient with a probability of 100%. If a setting of the at least one operating parameter led to an improvement of a health state of a patient but did not result in such improvement with another patient, the positivity value may be 50%. Alternatively, the positivity value may also be scaled to an interval of −1 and 1 (or −100% to +100%), with −1 indicating a deterioration of the health state of the patient and 1 indicating an improvement of the health state of the patient. The positivity value may also be based on a binary value set (e.g., − and +) or any other suitable value set.

In an exemplary scenario, a stored profile may be selected as described herein. Subsequently, the positivity value may be compared with a respective positivity threshold for the positivity value (which may be different from the threshold for the metric). If the positivity value exceeds the threshold, the selected stored profile may ultimately be selected as it may most certainly lead to an improvement of the health state of the patient. If the positivity value of the selected profile is below the positivity threshold, the profile may ex nunc be rejected as it may likely not lead to the desired improvement of the health state of the patient. In such a scenario, a further stored profile may be selected, e.g., the profile whose metric exhibits the second best minimum and/or the profile whose metric is below the threshold (as outlined above). Then, the respective positivity value of the further stored profile may be compared to the positivity threshold. If the positivity value exceeds the value of the positivity threshold, it may ultimately be selected. Alternatively, the calculation of the metric may a-priori be limited to stored profiles with positivity values above the positivity threshold.

The comparing of the generated profile for the patient with stored profiles may lead to settings which are found in more than one stored profile. If, in addition, several or all of these multiple stored profiles are also equipped with a positive positivity value (indicating an expected improvement of the health state of the patient based on the settings), the settings (associated with the stored profiles) may be interpreted as more reliable. In other words, if multiple stored profiles, which comprise the same settings are assigned with a positivity value which indicates that the related settings for the medical device have (historically) led to an increase of the health state of the patient, the setting for the medical device may be seen as more reliable due to the increased statistical support. Therefore, a stored profile may not only be selected based on requiring a certain positivity value but also based on a certain statistical support (i.e., the settings must have led to a positive result for various profiles). The statistical support may comprise requiring that at least two, three, four, five, and/or ten different stored profiles need to be assigned with a positive positivity value (e.g., at least 50%). Alternatively, it may also be possible that the selection requires that a certain setting for the medical device has led to an improvement of the health of the patient with a certain frequency, e.g., in more than 80%, more than 90%, more than 99% or more than 99.9% of all stored profiles comprising these settings.

The apparatus may further comprise means for obtaining feedback for the setting and may comprise means for determining a positivity value for the setting based on the feedback. Additionally, the apparatus may comprise means for generating an updated profile for the patient including the positivity value and the setting. Further, the apparatus may also comprise means for storing the updated profile in the storage medium. This way, further stored profiles may be generated that will be available for future optimization of the medical device of the patient and/or of medical devices of other patients. In this way, based on data from a multitude of patients that may be continuously updated, medical devices may be adjusted in an optimized manner.

In addition to storing the updated profile, the positivity value determined for the updated profile may also be used to adjust the positivity value of the stored profile whose stored setting was selected. For example, if the patient's health state improved (deteriorated) after adjusting the medical device to the setting, the positivity value of the stored profile whose setting was selected may be increased (reduced). Still, additionally or alternatively, it is conceivable to generate a cumulative stored profile, e.g., a profile which includes the selected setting and which includes two (or more) (sets of) patient-specific values: that of the generated updated profile and that of the already stored profile. Then, an average positivity for the selected setting and the two (or more) (sets of) patient-specific values may be stored in the cumulative profile.

In some examples, the storage medium may be a blockchain, and the updated profile may be stored therein. Storing the updated profile in a blockchain may in particular provide the advantage of increasing the data integrity and redundancy (as outlined above) associated with the updated profile. The storage medium may also be any other database, or any other suitable storage medium.

The means for obtaining feedback for the setting may comprise means for receiving an update of the patient-specific value of the at least one parameter (or repeatedly receiving updates), and the means for determining a positivity value may be adapted to determine a positivity value based on the updates. This may provide the advantage of enabling a monitoring of the health state of the patient in response to the altering of the medical device to the setting. For example, monitoring the patient-specific value of the at least one parameter may be used to derive a change of the health state of the patient in response to altering the medical device to the setting. For example, it may be discerned whether a patient's heartbeat returns to a more regular shape and/or a heart rate within a preferred range (or whether this was not the case or whether there was even a deterioration).

Feedback may comprise direct feedback, e.g., input via user interface e.g., of a smartphone app (e.g., a patient may confirm that the current settings of the medical device are experienced as comfortable and/or medical staff monitoring the patient may confirm the current settings as positive). The feedback may be forwarded to the apparatus and received by the apparatus via an interface, as described herein. The feedback may also comprise further patient-specific values parameters (e.g., a change of a pulse rate towards an interval which is considered as (more) healthy) and/or the absence of a deterioration of the health state of the patient, e.g., by means of an absence of a deviation of the patient-specific value from the interval which is regarded as healthy (e.g., a change of the pulse rate to 180 bpm at rest). These may be obtained from the medical device, or other devices, as described herein.

Feedback may also be received by means of a check-up (e.g., at a hospital) or a telemetric remote request (e.g., by means of a wireless request which may occur over the internet). It is desirable to store any kind of received feedback to iteratively train the apparatus and to thus allow a convergence of the health state of the patient towards an optimized state (i.e., which is experienced as comfortable and/or which is regarded as healthy).

Regardless of the source of feedback, the positivity value may exemplarily be assigned with a value in between 0% and 100% (or −100% and 100%), wherein the value may be understood as a level of improvement (or deterioration) of the health state of the patient.

The means for generating an updated profile for the patient including the positivity value and the setting may also be adapted to include in the updated profile, the patient-specific value of the at least one parameter. Additionally, also possible updates of the value(s) may be included in the updated profile.

The apparatus may further comprise means for initializing the device with the setting and/or for altering the medical device to the (second) setting. Hence, a fully closed-loop adjustment of the medical device may be provided.

Additionally of alternatively, the apparatus may further comprise means for providing the setting to medical staff and/or the patient. Prior to initializing/altering a medical device to the setting, it may be beneficial to consult with the medical staff and/or the patient. The consultation may allow to verify that the setting is not harmful to the health state of the patient. Such a conclusion may be based on the experience of a medical staff and/or the subjective feeling of the patient. The patient and/or medical staff may instruct the apparatus to implement the setting and/or they may manually implement the setting.

For example, the apparatus may be adapted to initialize/alter the medical device to the setting, if the positivity value of the stored profile with this setting exceeds a first threshold and/or if the metric between the generated profile for the patient and the stored profile with this setting is below a second threshold. Additionally or alternatively, the apparatus may provide the setting to medical staff and/or the patient, before altering the setting of the medical device, if one or both of the above conditions are not met and/or if the stored profile with this setting was only found after recalculating the metric for an augmented profile for the patient. Additionally or alternatively, the consultation with medical staff and/or the patient, before initializing/altering the setting of the medical device, may also occur on an irregular basis and may act as an additional control mechanism of the therapy and/or diagnostic based on a random sample. If the medical staff and/or the patient reject the setting, it may finally be discarded.

The present disclosure further comprises a method for determining settings of a medical device associated with a patient. The method may comprise the step of receiving a patient-specific value of a least one parameter (characterizing a state of the patient). It may include the step of generating a profile for the patient based on the patient-specific value. And it may include the further step of determining a setting of at least one operating parameter of the medical device based on a comparison of the profile for the patient with stored profiles of the patient and/or of other patients in a storage medium, each stored profile comprising a stored setting of the at least one operating parameter and a stored patient-specific value of the at least one parameter.

The method may further comprise one or more of the steps described herein, even if they are specifically described with respect to an apparatus.

The present disclosure further comprises a computer program which may comprise instructions which may cause a computer to implement the method steps described herein, and/or the means as described herein, when the instructions are executed.

Whether described as method steps, computer program and/or means, the functions described herein may be implemented in hardware, software, firmware, and/or combinations thereof. If implemented in software/firmware, the functions may be stored on or transmitted as one or more instructions or code on a computer-readable medium. Computer-readable media includes both computer storage media and communication media including any medium that facilitates transfer of a computer program from one place to another. A storage medium may be any available media that can be accessed by a general purpose or special purpose computer. By way of example, and not limitation, such computer-readable storage media can comprise RAM, ROM, EEPROM, FPGA, CD/DVD or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor.

It is further noted that the present invention is not limited to the specific feature combinations expressly listed herein, which are only understood as examples. Other features and/or feature combinations may also be possible.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The following FIGURE is provided to support the understanding of the present invention:

FIG. 1 Illustration of a flow chart of a possible implementation of a closed loop apparatus/method according to the present disclosure.

DETAILED DESCRIPTION

The following detailed description of the present invention and further embodiments described therein are provided to facilitate the understanding of the present invention.

FIG. 1 shows a flow diagram of an exemplary embodiment of the steps carried out by an apparatus or a method according to the present disclosure. A state of a patient 1 is described by at least one patient-specific value of at least one parameter $x_1, \ldots, x_n$. The at least one parameter may represent at least one of a cardiovascular parameter (e.g., blood pressure, pulse rate) and/or a cardio pulmonal parameter (e.g., a blood oxygen concentration), body temperature or any other patient-specific vital parameter. Alternatively, the at least one patient-specific value may at least be based on entries in a database, a patient chart (e.g., at least one of the above-mentioned parameters and/or further a detailed list of the administered medication, potential allergies and intolerances of the patient, an anamnesis, reports regarding earlier hospitalization, etc.), data of an implanted device (e.g., a pacemaker, an implanted defibrillator, a cochlea implant, etc.). Further data sources may comprise a hospital information system (e.g., all information processing devices and systems in a hospital which may e.g., comprise doctors' letters, surgery reports, etc.), clinical data sets (e.g., information related to the health state of the patient, e.g., blood values, and further parameters which cannot directly be gained by means of sensors, e.g., the subjective wellbeing of the patient). Additionally or alternatively, patient-specific data may also be retrieved over the internet, e.g., a GPS location of a patient and related environmental data (e.g., a temperature value, a humidity value, etc.) and/or from a blockchain.

A medical device 2, as described herein, may possess at least one current setting of at least one operating parameter $y_1, \ldots, y_n$. The at least one setting may e.g., be related to a level of a medication dose, a clock signal for e.g., a pacemaker, an oxygen flow, etc. In case of initialization of medical device 2, such current setting may not exist.

A patient-specific profile 3 may be generated based on the at least one patient-specific value of the at least one parameter (and the at least one setting of the at least one operating parameter, if available). The patient-specific profile may be understood similarly as a flashcard which comprises at least one parameter that may characterize (a state of) the patient (encoded as the at least one patient-specific value) and the corresponding setting of the medical device (if any). The generated patient-specific profile 3 may additionally be assigned with a patient-specific ID. A patient-specific ID may be understood as a distinct (but anonymous) indicator used to unambiguously identify a patient. The patient-specific profile 3 may either be generated once per patient and may comprise a temporal evolution of the at least one patient-specific value which e.g., facilitates the evaluation whether an applied treatment has led to a desired change of the at least one patient-specific value. Alternatively, it may also be possible that the patient-specific profile 3 only comprises a snapshot of the current at least one patient-specific value and the corresponding at least one setting of the medical device. By additionally assigning a patient-specific ID to the generated patient-specific profile 3, it may ex post be possible to assign the at least one patient-specific profile 3 to the respective patient.

The generated patient-specific profile 3 may further be compared to at least one stored profile 4. The at least one stored profile 4 may be based on evidence-based (historic) data sets, may relate to the same patient or at least one other patient as described above. The comparing may e.g., comprise a comparison of the at least one patient-specific value of the generated patient-specific profile to a stored patient-specific value in the at least one stored profile. The comparison may also comprise a calculation of at least one metric between the at least one patient-specific value of the generate patient-specific profile and the stored patient-specific value in the at least one stored profile, which may be understood as the calculation of a difference between the respective values. A stored profile and the generated patient-specific profile may be understood as "similar" or "matching" if the calculated difference is below a threshold. The threshold may be a pre-defined value, identical for all patients, or may be a subjective value which is particularly chosen for a certain patient. The latter may in particular be used to consider pre-existing diseases which may e.g., cause a ubiquitous offset of the blood pressure of the patient with respect to a blood pressure which is generally regarded as normal and healthy. If two profiles are considered as similar, the similar stored profile may be selected.

Each stored profile may also comprise a positivity value which represents a likelihood that the associated at least one setting may yield to an improvement of the health state of the patient. A selected stored profile may only be further processed if the positivity value is above a threshold wherein the threshold may be defined by the medical staff and/or the patient.

The setting of the selected profile may then be used by the apparatus to automatically adjust/initialize the medical device 2 accordingly. Alternatively, the selected profile may be presented to a member of the medical staff and/or the patient. The medical staff and/or the patient may be asked to confirm the at least one setting associated with the selected stored profile prior to altering the medical device 2 to the at least setting associated with the selected stored profile. The medical staff and/or the patient may also reject the selected profile if it is, e.g., expected that the profile would not lead to an improvement of the health state of the patient and/or may be considered as dangerous.

The setting of the selected stored profile may be used to generate an updated profile 5, including this setting and the patient-specific value of the at least one parameter of the generated profile 3 for the patient. After setting the medical device 2 to the selected setting, at least one patient-specific value may be retrieved from the patient 1, e.g., by means of a blood pressure measurement.

After setting the medical device 2 to the selected setting, the at least one value may be retrieved repeatedly (e.g., periodically or quasi-periodically as described above) or may only be retrieved once. It may automatically be detected whether the setting has led to an improvement of the health state of the patient, e.g., if the measured blood pressure has returned into an interval which is considered as not harmful/healthy for the patient. Additionally or alternatively, this assessment may be made by means of an external confirmation whether the setting has led to an improvement of the health state of the patient. This may comprise the subjective feeling of the patient and/or may be based on the experience of the medical staff. An updated profile 6 (comprising the least one patient-specific value, possibly update(s) thereof, a setting and optionally the positivity value) may be then be generated and stored together with the at least one stored profile 4.

If it is detected that the setting deteriorates the state of the patient, the medical device 2 may either be set to the preceding setting or may be set to a default value which may e.g., be defined by the medical staff and/or the patient. It may also be possible that the updated profile 6 is stored, even if it deteriorates the health state of the patient. In such a case, the positivity value may be assigned accordingly (i.e., may be assigned with a value that indicates the deterioration). Hence, the updated profile 6 (which deteriorates the health state of the patient), may be recognized as potentially harmful for the patient if it is selected in any of the future iterations of the described sequence. For example, all other patients (and/or their medical staff, and/or medical devices) using these settings may be alerted immediately. Specifically, a selected setting may be cross-checked for profiles indicating this setting as harmful. If this cross-check results in a hit, it may also be provided to the medical staff/patient, and/or the setting may not be used for adjusting the setting of the medical device.

If the comparison of the generated patient-specific profile 3 with the at least one stored profile 4 does not result in a "match" (e.g., if no suitable stored profile can be determined whose calculated metric is below a pre-defined threshold), an augmented patient-specific profile 7 may be generated. The augmented patient-specific profile 7 may comprise the generated patient-specific profile 3 but may further comprise at least one additional parameter associated with the state of the patient. By means of including the at least one additional parameter, it may be possible to explain the at least one difference (i.e., the reason why no stored profile can be found which represents a "match" to the generated profile 3) between the generated profile 3 and the at least one stored profile.

After generating the augmented profile 7, a new comparison between the augmented profile and the at least one stored profile may occur. The comparison may comprise the calculation of at least one metric. If a match can be found, the stored setting of the stored profile that represents the "match" is selected, and an updated profile 8 may be generated. Then, the flow may proceed similarly as described above with reference to updated profile 5. Specifically, the medical device 2 may be altered to the setting associated with the augmented profile 7, and at least one patient-specific value of the at least one parameter may repeatedly be retrieved from the patient 1, e.g., at least one patient-specific value may be retrieved from the patient 1, e.g., by means of a blood pressure measurement. The at least one value may be retrieved repeatedly (e.g., periodically or quasi-periodically as described above) or may be retrieved once. Based on the retrieved data, it may either be decided automatically whether the at least setting has led to an improvement of the patient or may be based on an external input, e.g., by means of the medical staff and/or the patient as described above (e.g., via an electronic device in communication with the apparatus).

If the at least one metric is still above a threshold, the augmented profile 7 may either be rejected as not applicable or may be presented to the medical staff and/or the patient requesting further input. Additionally or alternatively, the patient may be presented with the advice to consult medical staff and/or the medical staff may be alerted to attend to the patient.

The sequence as described above may be executed once or may be executed repeatedly in a closed loop sequence as described above.

In an exemplary embodiment, the aspects described herein may be implemented to optimize the setting of an active implant, such as e.g., a pacemaker or an implanted defibrillator (ICD).

In the beginning, when implanting the implant, a new profile may be generated for the patient. The profile may comprise characterizing information of the patient, e.g., anamnesis related parameters (as described above), a patient-ID (as described above), etc., and may be used to track the temporal evolution of patient-specific values of at least one parameter (e.g., a pulse rate).

After generating the profile for the patient, the generated profile may be compared with stored profiles (which may be assignable by means of a patient-specific ID) of the same patient (a historic profile of the patient) and/or with profiles of other patients. The comparison may involve a determination of similarities between the generated profile for the patient and the stored profiles (as described above). The stored profiles may comprise settings for at least one operation parameter for the implant (e.g., the pacemaker) associated with a patient-specific value of at least one parameter. In other words, the stored profiles may comprise a profile for a patient with a similar age, similar pre-conditions (e.g., no or the same pre-existing conditions) with settings that are positively confirmed. That stored profile may be selected as described herein based on a comparison of the generated profile for the patient (preferably based on rank one similarities as described above). The implant may then initially be set using the settings in selected stored profile. Therefore, the initial setting of the at least one operating parameter of the pacemaker may be based on evidence-based profiles.

The apparatus may either forward the settings which were gathered from the stored profile to the medical device which may thus be automatically set. The settings may additionally or alternatively be forwarded to the patient and/or medical staff (e.g., via the medical device or another device as described herein) and the settings are then implemented manually and/or automatically after confirmation of the setting by medical staff and/or patient.

If the settings are used for setting the medical device, they may be saved to the generated profile for the patient. Additionally, the generated profile for the patient may also be equipped with a positivity value (as described above). For example, if the settings are confirmed by the patient and/or medical staff, the positivity value may be assigned with a value indicating that the setting may be regarded as beneficial for the patient.

However, it may also be possible that the medical staff and/or the patient intend a deviation from the settings as forwarded by the apparatus. In such a case, the extracted settings may be stored in the generated profile with a positivity value which indicates that the setting may be harmful and/or not applicable for the patient. The overwritten settings (by the medical staff and/or the patient) may be stored in the generated profile with a positivity value indicating the settings as beneficial for the patient. This step supports a self-learning functionality of the present invention.

Also if settings are confirmed or altered during a regular check-up by medical staff and/or the patient (or after an alert), the profile may be updated and the settings' positivity value may be adjusted accordingly. For example, it may be further increased, if the settings are confirmed or it may be reduced if the settings are altered.

After the initialization of the medical device, the apparatus may (e.g., as described herein, for example, continuously/repeatedly, in real-time, e.g., once per second) receive patient-specific values for the at least one parameter which may be measured by a sensor system, e.g., of the medical device (e.g., of the pacemaker), such as a pulse rate. The received values may be used to generate updated profiles (e.g., in real-time) for the patient which may be compared to stored profiles and/or the initially generated profile. The latter may allow a tracking of the evolution of the health state of the patient and may allow an early detection of a decline of the health state of the patient, e.g., if a certain threshold (a pre-defined interval of a pulse rate) is exceeded. In the latter case, a comparison with stored profiles may possibly only follow once the updated profile (at least one parameter value) deviates from the initially generated profile (corresponding parameter value(s)) by more than a predetermined threshold. In both cases, the comparison of patient-specific values with stored respective values may allow to readjust the settings of the medical device, based on stored settings which have improved the health state of patients in the past.

If the repeatedly occurring receiving of the patient-specific value indicates a change of the health state of the patient which may indicate a malfunction of the pacemaker (or sub-optimal settings), e.g., as determined by a comparison with initial and/or stored profiles, the deviation may be saved to the generated profile for the patient along with a respective positivity value (indicating the malfunction). In such a case, a comparison of the generated profile for the patient with stored profiles may be performed with the goal of determining a respective setting for the pacemaker which is more suitable for the patient. Alternatively, upon a corresponding alert, the medical staff and/or the patient may set a new setting for the pacemaker which may then be stored to the generated profile for the patient.

It is also conceivable that an alert is sent to the medical device, patient and/or medical staff, if for another profile for another patient a deterioration is detected. An alert may then be sent to all medical devices (associated patients and/or medical staff) which use similar settings as stored in the profile for which a deterioration was detected.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An apparatus for determining settings of a medical device associated with a patient, comprising a processor operatively associated with a non-transient storage medium, an interface, and a data source, the apparatus configured for:

a) receiving a patient-specific value of a least one parameter;

b) generating a profile for the patient based on the patient-specific value; and c) determining a setting of at least one operating parameter of the medical device based on a comparison of the profile for the patient with stored profiles of the patient and/or of other patients in a storage medium, each stored profile comprising a stored setting of the at least one operating parameter and a stored patient-specific value of the at least one parameter, wherein determining the setting involves:

selecting a stored profile based on a comparison of the stored patient-specific value of the at least one parameter in the stored profile and the patient-specific value of the at least one parameter in the generated profile for the patient; and selecting the stored setting of the at least one operating parameter of the selected stored profile as the setting;

d) calculating a metric for the stored profile, wherein the metric is calculated between the value of the at least one parameter in the generated profile for the patient and the stored patient-specific value of the at least one parameter in the stored profile, wherein the calculating is adapted to calculate a metric for a plurality of the stored profiles, and the selecting is adapted to select a stored profile for which the metric is minimized, wherein the selecting the stored profile is adapted to select the stored profile if the metric is below a threshold;

e) augmenting the generated profile for the patient with at least one further patient-specific value of at least one further parameter if none of the stored profiles has a metric below the threshold;

f) calculating an augmented metric for the stored profiles, wherein the augmented metric is calculated between the patient-specific values in the augmented profile for the patient and corresponding stored patient-specific values in the stored profiles.

2. The apparatus according to claim 1, wherein the receiving the one or more patient-specific value comprises receiving an update of the at least one patient-specific value.

3. The apparatus according to claim 2, further configured for:

updating the profile for the patient based on the update of the at least one patient-specific value; and determining a second setting of the at least one operating parameter based on a comparison of the updated profile for the patient with stored profiles of the patient and/or of other patients in a storage medium, each stored profile comprising a stored setting of the at least one operating parameter and a stored patient-specific value of the at least one parameter.

4. The apparatus according to claim 1, wherein selecting the stored profile further comprises selecting the stored profile based on a positivity value associated with the stored profile.

5. The apparatus according to claim 1, wherein the apparatus is configured for:

obtaining feedback for the setting;

determining a positivity value for the setting based on the feedback; and generating an updated profile for the patient including the positivity value and the setting;

storing the updated profile in the storage medium.

6. The apparatus according to claim 5, wherein the apparatus is adapted to receive an update of the patient-specific value of the at least one parameter, and determining the positivity value comprises determining the positivity value based on the update.

7. The apparatus according to claim 5, wherein storing the updated profile comprises storing the updated profile in a blockchain.

8. The apparatus according to claim 1, wherein the apparatus is further configured for providing the setting to medical staff and/or a patient and/or for altering the medical device to the setting.

9. Method for determining settings of a medical device associated with a patient, the method comprising:

a) receiving a patient-specific value of a least one parameter;

b) generating a profile for the patient based on the patient-specific value;

c) determining a setting of at least one operating parameter of the medical device based on a comparison of the profile for the patient with stored profiles of the patient and/or of other patients in a storage medium, each stored profile comprising a stored setting of the at least one operating parameter and a stored patient-specific value of the at least one parameter, wherein determining the setting involves selecting a stored profile based on a comparison of the stored patient-specific value of the at least one parameter in the stored profile and the patient-specific value of the at least one parameter in the generated profile for the patient, and selecting the stored setting of the at least one operating parameter of the selected stored profile as the setting;

d) calculating a metric for the stored profile, wherein the metric is calculated between the value of the at least one parameter in the generated profile for the patient and the stored patient-specific value of the at least one parameter in the stored profile, wherein the calculating is adapted to calculate a metric for a plurality of the stored profiles, and the selecting is adapted to select a stored profile for which the metric is minimized, wherein the selecting the stored profile is adapted to select the stored profile if the metric is below a threshold;

e) augmenting the generated profile for the patient with at least one further patient-specific value of at least one further parameter if none of the stored profiles has a metric below the threshold; and f) calculating an augmented metric for the stored profiles, wherein the augmented metric is calculated between the patient-specific values in the augmented profile for the patient and corresponding stored patient-specific values in the stored profiles.

10. Computer program comprising instructions which cause a computer to implement the steps of claim 9, when the instructions are executed.

* * * * *